(12) United States Patent
Falkvall et al.

(10) Patent No.: US 6,666,840 B1
(45) Date of Patent: Dec. 23, 2003

(54) METHOD FOR DETERMINING WASTE PRODUCTS IN THE DIALYSIS LIQUID IN DIALYSIS TREATMENT

(75) Inventors: Thore Falkvall, Helsingborg (SE); Lars-Olof Sandberg, Ronneby (SE); Ivo Fridolin, Linkoping (SE); Lars-Goran Lindberg, Bankekind Haga (SE)

(73) Assignee: Althin Medical AB, Ronneby (SE)

( * ) Notice: Subject to any disclaimer, the term of this patent is extended or adjusted under 35 U.S.C. 154(b) by 0 days.

(21) Appl. No.: 09/700,849

(22) PCT Filed: Jun. 4, 1999

(86) PCT No.: PCT/SE99/00976

§ 371 (c)(1),
(2), (4) Date: Apr. 30, 2001

(87) PCT Pub. No.: WO99/62574

PCT Pub. Date: Dec. 9, 1999

(30) Foreign Application Priority Data

Jun. 4, 1998 (SE) .............................................. 9801983

(51) Int. Cl.[7] ........................... A61M 37/00; C02F 1/44
(52) U.S. Cl. ..................... 604/5.04; 604/6.09; 210/645; 210/646; 210/647
(58) Field of Search .............................. 604/4.01, 5.04, 604/6.09, 6.11, 28, 31; 210/645–647

(56) References Cited

U.S. PATENT DOCUMENTS

| | | | |
|---|---|---|---|
| 4,244,787 A | | 1/1981 | Klein et al. |
| 4,904,237 A | * | 2/1990 | Janese ........................... 604/28 |
| 5,110,477 A | * | 5/1992 | Howard et al. ........ 210/321.65 |
| 5,518,623 A | * | 5/1996 | Keshaviah et al. ......... 210/646 |
| 5,644,402 A | | 7/1997 | Chevallet |
| 5,730,712 A | * | 3/1998 | Falkvall et al. .......... 210/321.8 |
| 5,788,846 A | * | 8/1998 | Sternby ................. 210/321.65 |
| 6,022,477 A | * | 2/2000 | Luo et al. .................... 210/645 |
| 6,110,384 A | * | 8/2000 | Goux et al. ................. 210/645 |

FOREIGN PATENT DOCUMENTS

| | | |
|---|---|---|
| DE | 39 00 119 C1 | 8/1990 |
| JP | 09149935 A | 6/1997 |
| WO | 94/08641 | 4/1994 |

OTHER PUBLICATIONS

Lindsay, et al., "Urea Monitoring During Dialysis: The Wave of the Future," vol. XXXVII, Trans. Am. Soc. Artif. Intern. Organs, 1991.

Dialyzer by ParaDigm Bio Technologies, Toronto, Canada.

Sansen, et al., "A Planar Conductimetric Sensor for Continuous Monitoring of Haemodialysis," IEEE Engineering in Medicine and Biology Society, 11th Annual International Conference, 1989.

* cited by examiner

*Primary Examiner*—Angela D. Sykes
*Assistant Examiner*—Leslie R. Deak
(74) *Attorney, Agent, or Firm*—Paula J. F. Kelly; Bell, Boyd & Lloyd LLC

(57) ABSTRACT

Method and device for determining in dialysis treatment the content of waste products in the outgoing dialysis liquid from the dialyzer. Measurement of the concentration of a certain substance or a combination of substances included in the waste products is effected spectrophotometrically directly on the outgoing dialysis liquid from the dialyzer. For that purpose there is provided after the dialyzer in or after the dialysing machine a measuring cell for spectrophotometric measurement. The measurement value obtained is multiplied by the flow of dialysis liquid for determining the content of said substance or said combination of substances in the outgoing dialysis liquid from the dialyzer.

13 Claims, 7 Drawing Sheets

Figure 1:
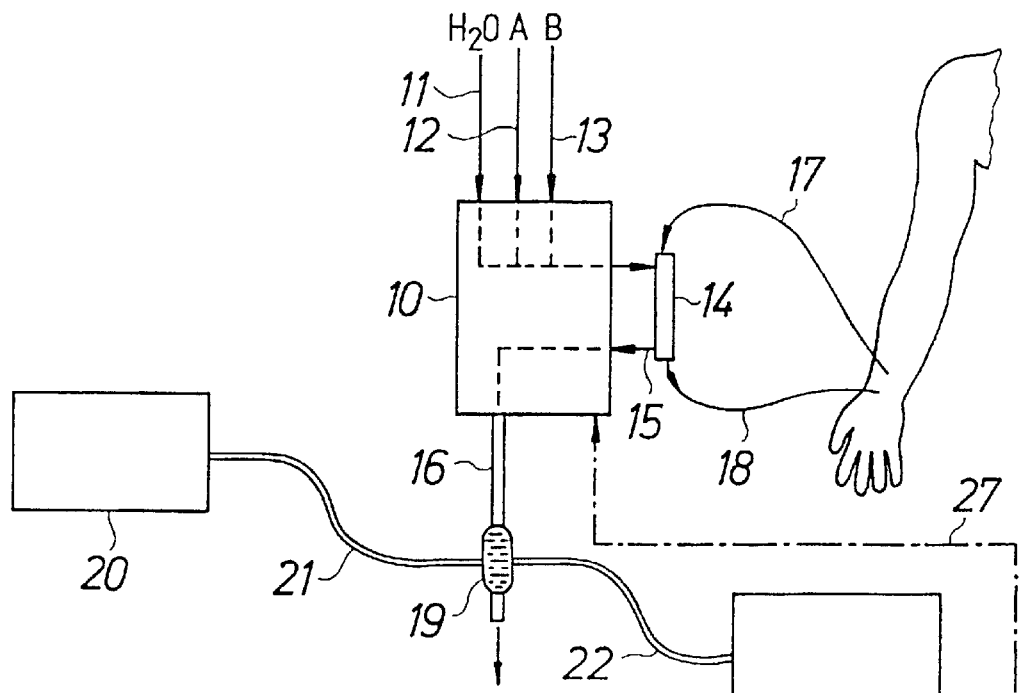

METHOD FOR DETERMINING WASTE PRODUCTS IN THE DIALYSIS LIQUID IN DIALYSIS TREATMENT

The invention relates to a method for determining waste products in the dialysis liquid in dialysis treatment.

Patients who have reduced kidney function or no kidney function at all get rid of waste products, including toxic substances, by dialysis treatment wherein the blood in an extracorporeal path via a membrane in the dialyzer is contacted with dialysis liquid containing different salts in such a concentration that the waste products by diffusion and convection pass through the membrane to the dialysis liquid and continue to a drain, the blood after having passed the dialyzer being returned to the patient.

The extent of the dialysis treatment that a patient shall be exposed to cannot be determined by feeling only; it is necessary to quantify in some way the result of the dialysis effect in order to avoid that the dialysis treatment will be insufficient. Considering that dialysis treatment is an expensive type of treatment, it is also just as important to avoid "overtreatment" of a patient. In other words, it is necessary to be able to control the efficiency of the dialysis treatment on-line, i.e. while the dialysis treatment is in progress, in order then to control manually or automatically the treatment by adjustment of the parameters of the dialysis machine in dependence thereof and thus to make the dialysis treatment more efficient.

In order to secure an adequate dialysis treatment the Kt/V(urea)-model has been developed (urea is one of the substances in the waste products used for measuring if an adequate treatment is offered), where K is the ability of the dialyzer to separate urea from the blood in ml/min, t is the treatment period in minutes, and V is the distribution of urea in the body in ml, which is related to the body weight of the patient. The non-dimensional factor Kt/V(urea) defines the reduction of the content of urea nitrogen in the blood and at three treatments each week should equal or be larger than 1 (at daily treatment the factor is lower than 1), and by using this factor it is possible to calculate the result of the treatment of the patient. The calculation of Kt/V(urea) is, however, complicated and requires that particularly the capacity of the dialyzer but also the accuracy of the dialysis machine and the distribution of the urea volume in the patient are accurately determined (Lindsay et al. *Urea Monitoring During Dialysis: The wave of the future, Vol. XXXVII—Trans Am Soc Arif Intern Organs* 1991). The Kt/V(urea) -model is used but is not considered absolutely reliable due to inherent sources of errors which are related to measurement values and product precision.

It has been recommended to combine the Kt/V(urea) model with continuous determined of the percentage reduction of urea in the patient during the dialysis treatment, and a proposal along this line is *Dianalyzer from Paradigm Biotechnologies*, Toronto, Canada. The device comprises a computer to which such quantities, i.a. Kt/V(urea), are supplied, which as required for calculation of the percentage reduction of urea (PRU) in the patient. A plasma sample is taken via a plasma filter from the extracorporeal blood path and is mixed with enzyme solution and reagent, the mixture obtained then being examined optically in order to determine the amount of urea in the blood, which in turn is used for determining the time at which the dialysis treatment in progress should be stopped. In Dianalyzer sampling is effected a certain number of times during the dialysis treatment and, thus, no continuous measurement of the urea reduction is concerned. In order to measure the urea reduction in the blood it is necessary to have parameters available which either must be established by blood analysis or have to be estimated, which makes this type of measurement unsuitable for application on-line. The development of this measuring method has been focused substantially on the development of suitable sampling devices in combination with traditional analysis instruments.

An apparatus which functions in a similar way with chemical reagents for determining of Kt/v is Biostat™ Urea Monitor from Baxter.

Monitoring of the urea content in the outlet flow of dialysis liquid provides greater flexibility as far as the applied measuring system is concerned, but so far the development has led up to manual sampling and the use of traditional measuring system. Samples of the dialysate therefor usually must be sent to a laboratory with the necessary measurement equipment.

Thus, it has been proposed (*IEEE Engineering in Medicine & Biology Society* $11^{th}$ *International Conference*) for continuous monitoring of hemodialysis to measure enzymatically induced conductivity changes caused by hydrolyse of urea (or other important molecules) in the dialysis liquid, especially developed sensors being used for such measurement. A drawback of these sensors is that they are cumbersome to calibrate and that it can be difficult to compensate for existing background conductivity.

The invention relates to method and dialysis machine for determining the content of waste products in the outgoing dialysis liquid wherein the measurement of the concentration of a certain substance or a combination of substances included in the waste products is effected directly on the outgoing dialysis liquid from the dialyzer at dialysis treatment. Method and machine of this kind are disclosed in US-A-4,244,787 and WO-A-9408641.

The purpose of the invention is to provide a method for accurate determination of the amount of waste products in the dialysis liquid during dialysis treatment, which allows application of a technique known per se and the use of a reliable apparatus set and which allows that urea or some other substance included in the waste products is measures so that one can choose to make the determination by measuring the substances which are best suited for the election of dialyzer and the control of the dialysis machine in order to adapt the dialysis treatment to the patient.

For said purpose the method according to claim 1 and the dialysis machine according to claim 13 are proposed according to the invention.

Figure 8:
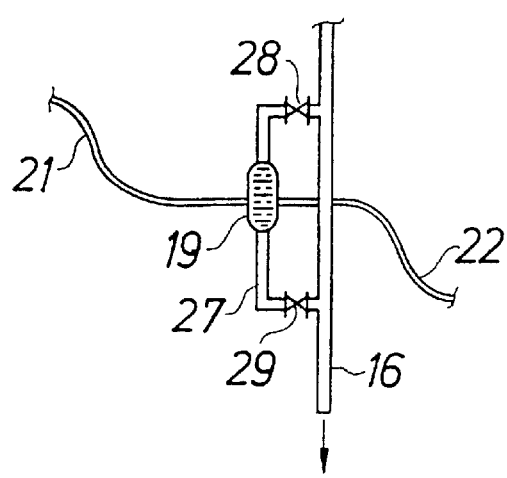
Figure 2:
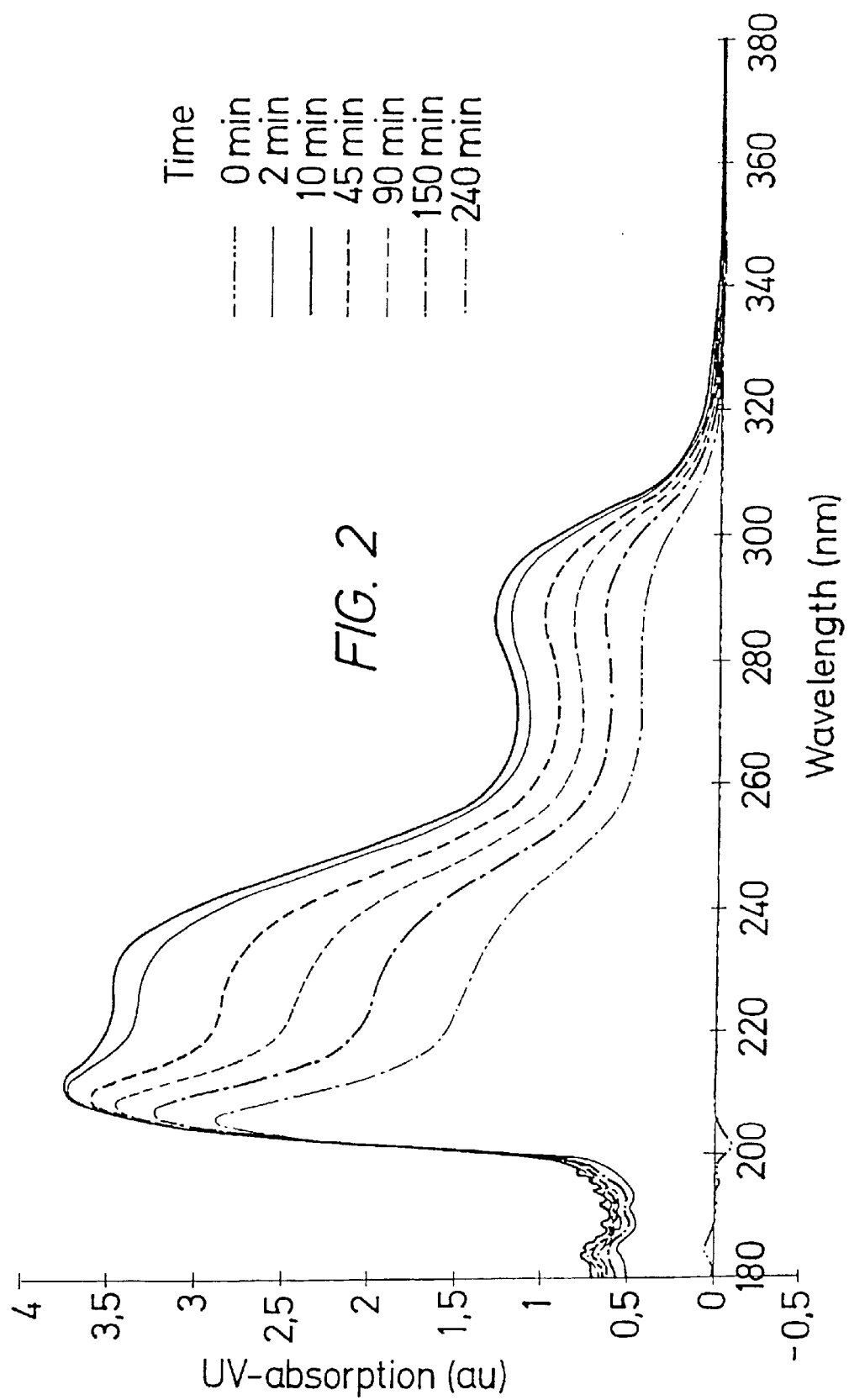
Figure 3:
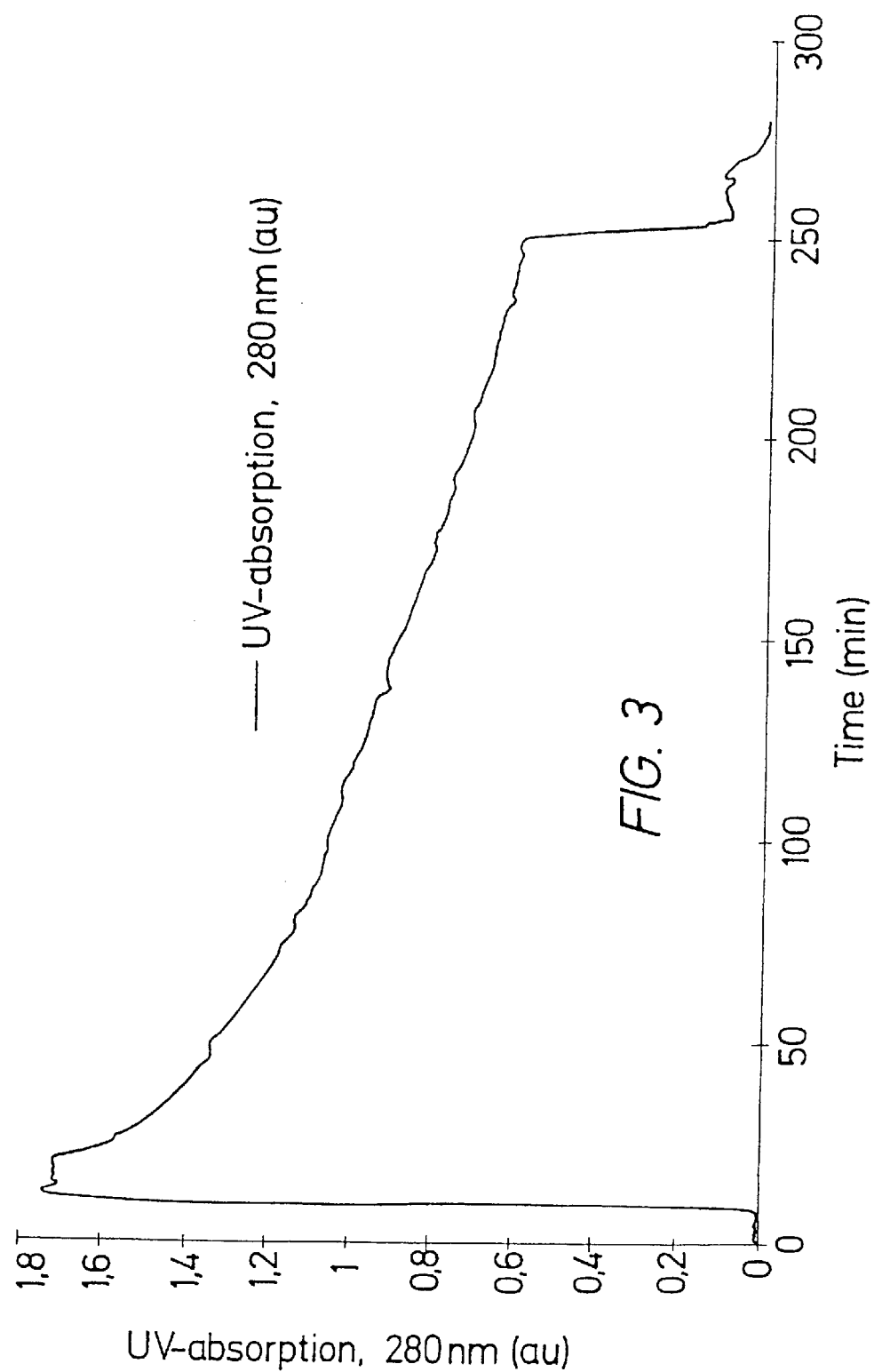
Figure 4:
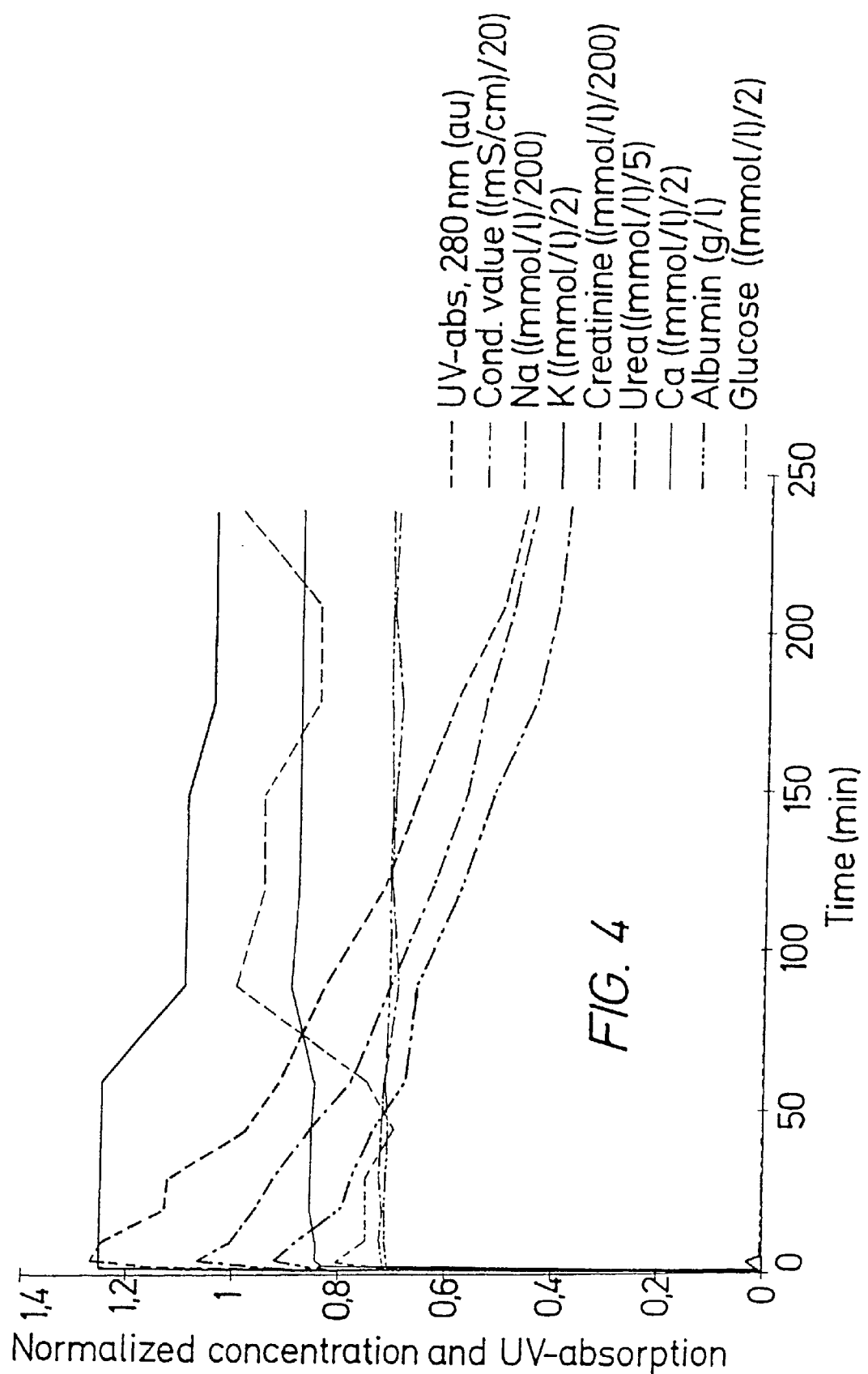
Figure 5:
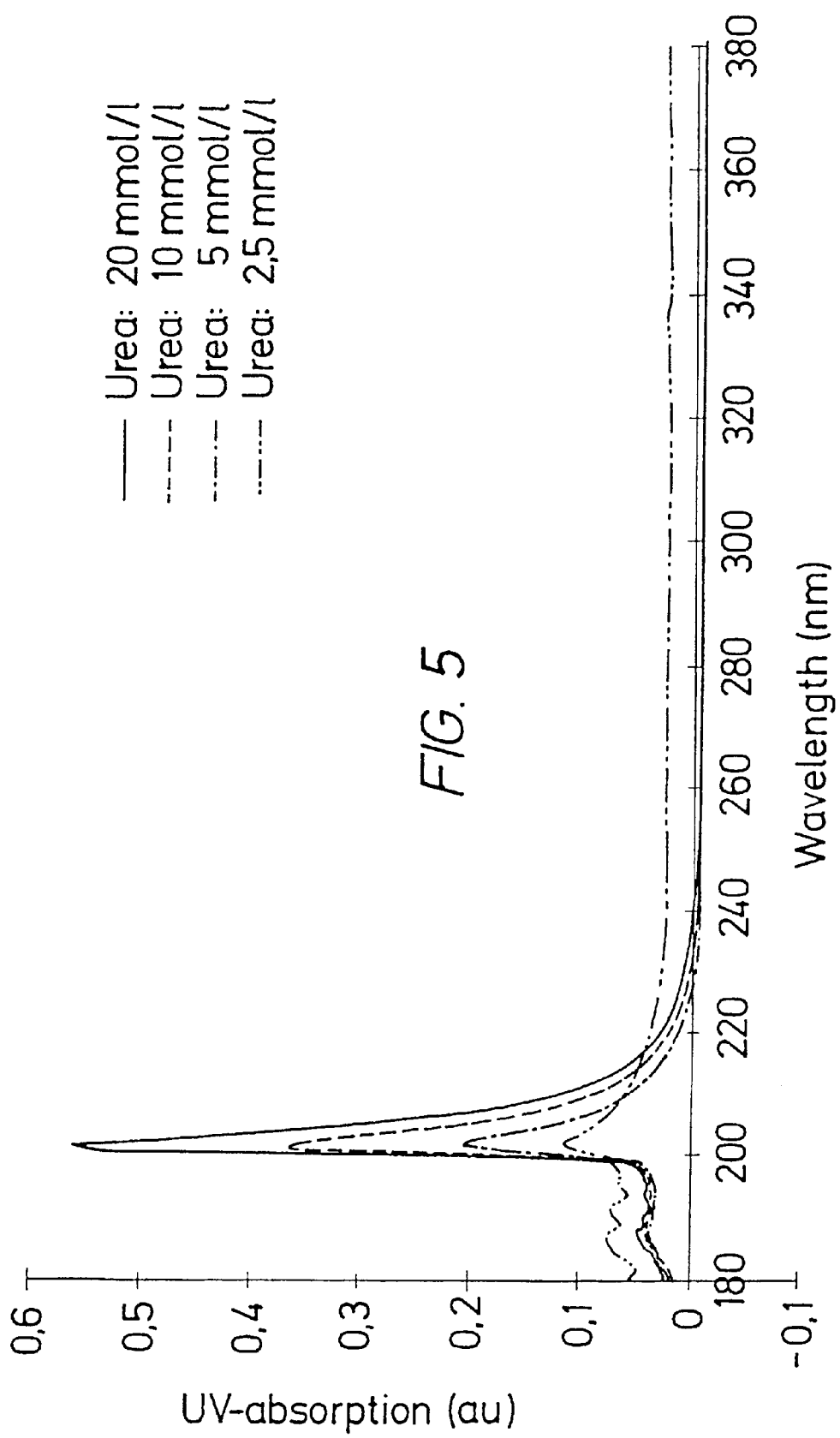
Figure 6:
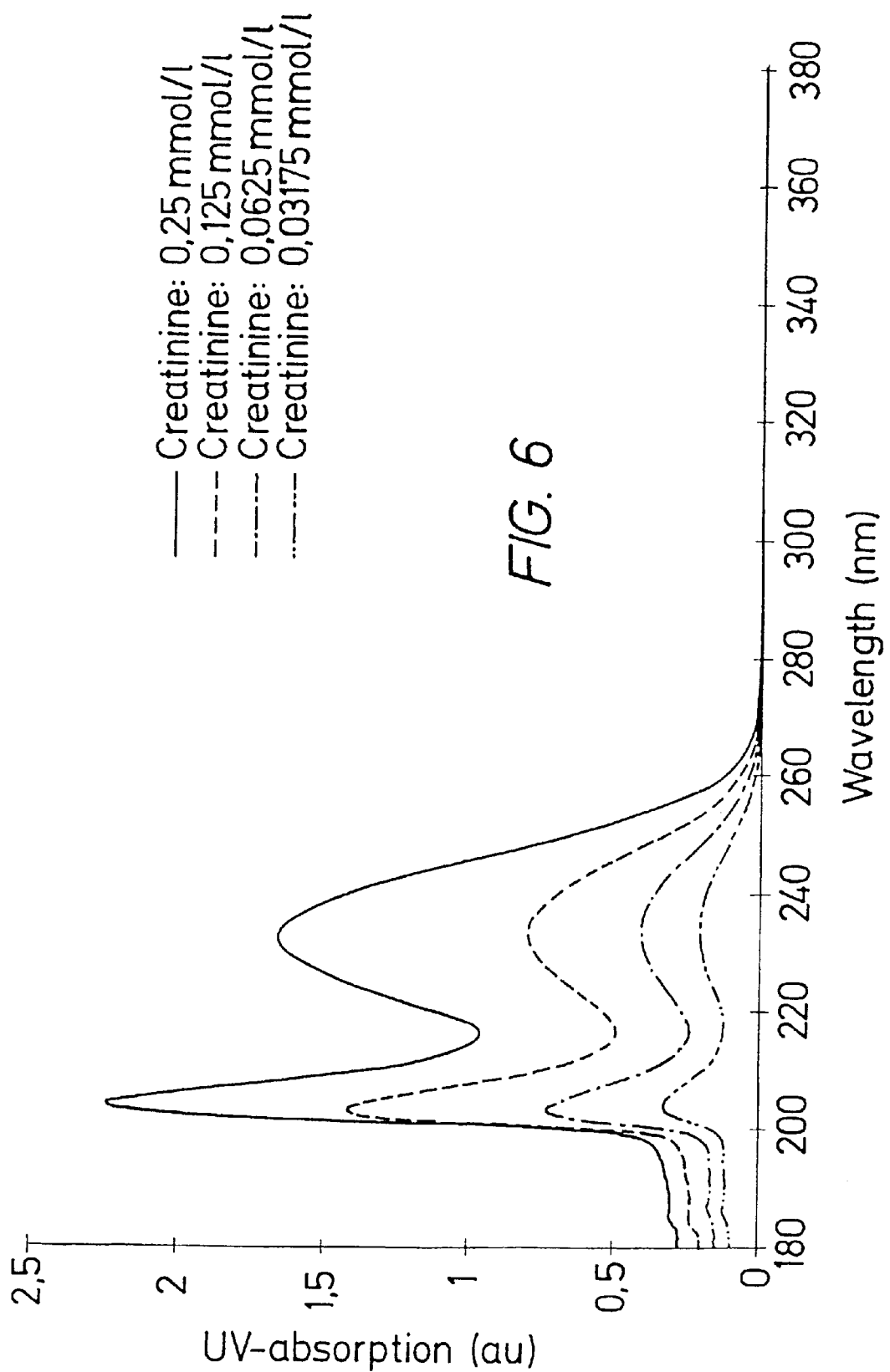
Figure 7:
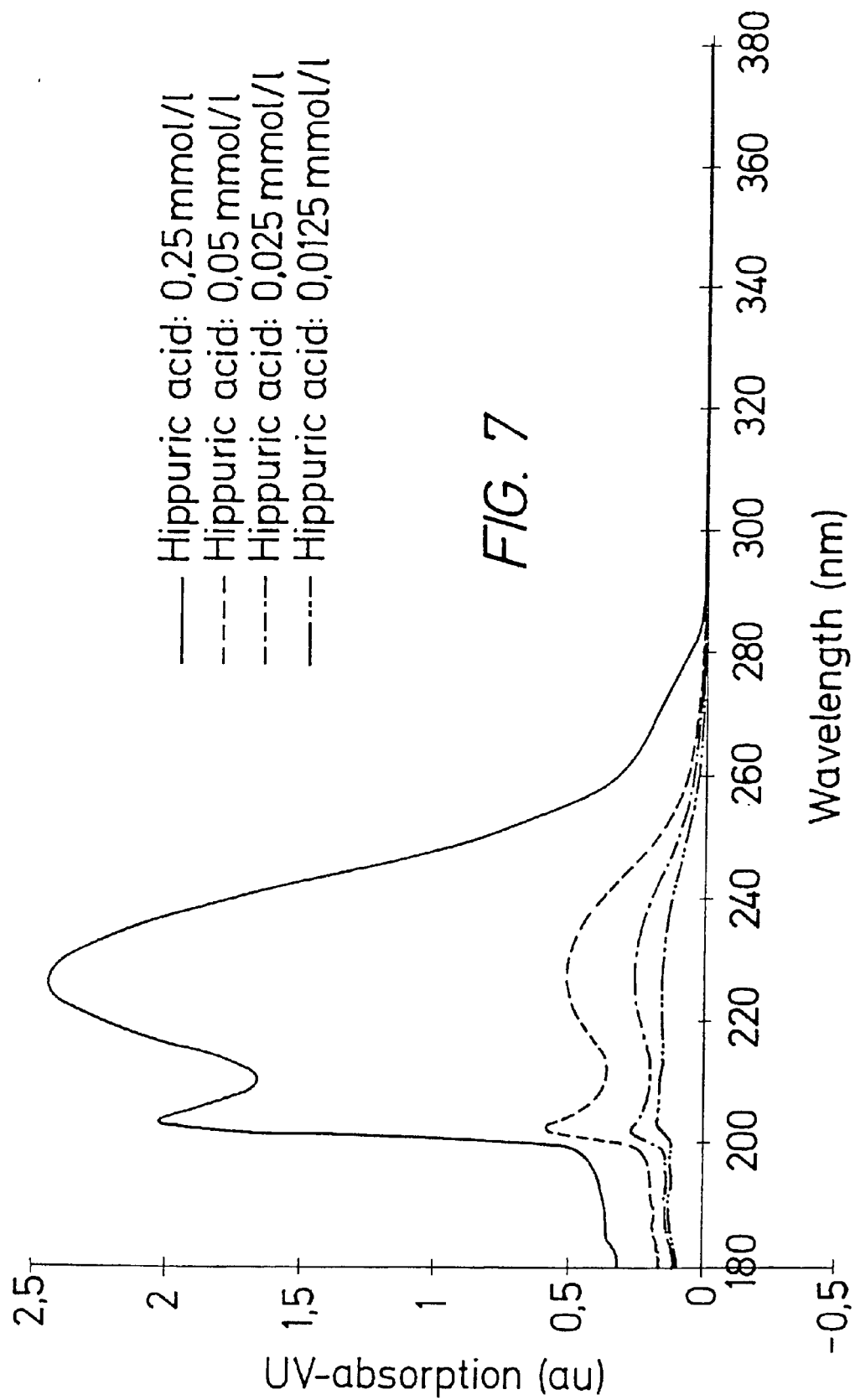

For description of the invention in more detail reference is made to the accompanying drawings in which FIG. 1 is a diagrammatic view of an analysis system with continuous (on-line) measurement of the amount of one or more substances included in the waste products removed from the dialyzer by the dialysis liquid, FIG. 2 is a diagram disclosing the absorption of waste products during a dialysis treatment at different wavelengths of the UV-light and at different times after the beginning of the dialysis treatment, FIG. 3 is a diagram showing the continuously recorded UV-absorption during a dialysis treatment for the wavelength 280 nm, FIG. 4 is a diagram disclosing the concentration of certain important substances in the waste products and has been established by measuring in a chemical laboratory, FIG. 5 is a diagram which discloses the variation in UV-absorption for urea at different wavelengths of the UV-light, FIG. 6 is a corresponding diagram as that in FIG. 4 for creatinine, FIG. 7 is a corresponding diagram as that in FIG. 4 for hippuric acid, and FIG. 8 is a partial diagrammatic view similar to that in FIG. 1 of a modified embodiment of the dialysis system.

The dialysis system disclosed in FIG. 1 comprises a dialysis machine 10 to which water is supplied at 11 and concentrates A and B at 12 and 13, respectively, for the production of dialysis liquid which is supplied to a dialyzer 14 at one side of the membrane therein and is drawn off from the dialyzer at the same side of the membrane at 15 in order to be supplied to a drain through a conduit 16. At the other side of the membrane the dialyzer 14 is connected to the blood system of a patient through a hose 17 for diverting blood to the dialyzer. The blood is returned from said other side of the membrane to the patient through a hose 18. The hose 17, the dialyzer 14, and the hose 18 thus form an extracorporeal blood path in which the blood via the membrane in the dialyzer contacts the dialysis liquid in order that waste products existing in the blood shall pass through the membrane to the dialysis liquid by diffusion and convection.

For continuous measurement of the concentration of a certain substance or a combination of substances included in the waste products in the outgoing dialysis liquid there is mounted somewhere on the outlet conduit 16 of the dialyzer after the dialyzer inside or after the dialysis machine a transparent measuring cell 19 to which UV-light is supplied from a light source 20 through an optic fibre 21. Light which is supplied to the measuring cell and passes through said cell and dialysis liquid passing therethrough will be absorbed and scattered in a varying degree by the waste products existing in the dialysis liquid so that increased concentration of a substance in the dialysis liquid reduces the light transmission. The light passing through is diverted by an optic fibre 22 to a photodetector 23 to be transformed therein to an electric signal which via an algorithm including multiplication of the measured concentration by the existing flow of dialysis liquid will be converted into a signal the value of which is related to the content of a single substance in the waste products or a combination of several substances.

The signal is supplied to a computer 24 with a display 25 for visualisation of the measurement result, and a printer 26 for printing of the measurement result.

In FIG. 1 a dot-and-dash line 27 indicates that the measurement result obtained can be transferred from the monitor to the dialysis machine for modification of the adjustment thereof as required by the measurement result.

The light absorption due to waste products in the dialysis liquid flowing from the dialysis machine has been registered during the dialysis treatment at different wave-lengths of the UV-light within the interval 180–380 nm, preferably 200–320 nm, by means of a spectrophotometer of the manufacture Kontron. The registration has taken place at different times after the beginning of the dialysis treatment, and the result is shown in FIG. 2. As will be seen the absorption is high, i.e. the concentration of waste products in the dialysis liquid is great, at the beginning of the dialysis treatment and then decreases continuously during 240 min. The continuously registered UV-absorption during a dialysis treatment is disclosed in FIG. 3 for the wavelength 280 nm.

In a chemical laboratory the concentration of certain important substances in the waste products, i.a. creatinine and urea, was measured and the measurement result is shown in FIG. 4. In the diagram shown therein, which discloses how the concentration of said substances varies over the time, also the UV-absorption at 280 nm is shown, and as will be seen, there is a good correlation between the graphs for urea and creatinine and the graph for UV-absorption.

The substances which occur as waste products in the dialysis liquid have been added to clean dialysate one at the time in concentrations which correspond to the concentrations existing in the dialysis liquid at dialysis, or higher, and spectrophotometric graphs have been recorded. As example there is shown in FIG. 5 the variation of the UV-absorption for urea, in FIG. 6 for creatinine and in FIG. 7 for hippuric acid. As will be gathered from the figures the absorption varies for different substances. Thus, the absorption is higher for urea between 200 and 220 nm, for creatinine between 200 and 260 nm, and for hippuric acid between 200 and 280 nm. This means that there is a possibility to differentiate between different substances in the dialysis liquid and to obtain specific sensibility for a certain substance which it is desired to monitor for determining the content of waste products in the dialysis liquid.

The object of the invention in the first place is to determine in a simple and reliable manner the content of waste products in the dialysis liquid in dialysis treatment in order that the patient by guidance thereof can be given an adequate dialysis treatment, but it is also possible to change in dependence of the measurement result the adjustment of the dialysis machine (feedback) in order to adapt the dialysis treatment to the special needs of the patient. By the possibility of choosing a certain substance for the monitoring of the dialysis treatment, exactly the substance can be chosen which is most suitable for the patient and is suitable for the election of dialyzer and the control of the dialysis machine.

In the described illustrative embodiment according to FIG. 1 the absorption of UV-light is measured, which passes through the outgoing dialysis liquid, but it is possible to measure instead according to known technique the UV-light which is reflected from the dialysis liquid. The light source 20, the measuring cell 19, and the photodetector 23 can be integrated to a unit except the optic fibres 21 and 22.

In the described embodiment the measurement on the dialysis liquid is effected continuously during the dialysis treatment but it is also possible to divert at intervals a minor quantity of the dialysis liquid and to measure on this quantity which is then sent to the drain. This sampling batch-wise can be totally automated. Such an embodiment is disclosed in FIG. 8. The measuring cell 19 is mounted in a shunt conduit 27 which is connected to the drain conduit 16 via a valve 28 at the inlet side of the measuring cell, and a valve 29 at the outlet side of the measuring cell. Valve 28 being open and valve 29 being closed a quantity of the outgoing dialysis liquid is taken from the drain conduit 16 into the measuring cell. After measuring on the dialysis liquid in the measuring cell as described above the valve 29 is opened to tap off the dialysis liquid in the measuring cell to the drain conduit. The valves as well as the measuring on the dialysis liquid in the measuring cell can be controlled automatically.

What is claimed is:

1. A method for determining a content of waste products in a dialysis liquid comprising the steps of: obtaining a measurement of a concentration of a certain substance or a combination of substances included in the dialysis liquid the measurement being obtained from outgoing dialysis liquid from a dialyzer during dialysis treatment, the measurement being determined spectrophotometrically; and a measurement value that is so obtained is multiplied by a flow rate of the dialysis liquid for determining the content of said substance or said combination of substances in the outgoing dialysis liquid from the dialyzer.

2. The method of claim 1, wherein the measurement is effected continuously on the dialysis liquid under flow.

3. The method of claim 1, wherein the measurement is effected regularly on a sample of the dialysis liquid taken under flow.

4. The method of claim 1 wherein the measurement is determined spectrophotometrically by means of UV-light.

5. The method of claim 4 wherein the UV-light includes a wavelength in the range 180–380 nm.

6. The method of claim 5 wherein the UV-light includes a wavelength in the range 200–320 nm.

7. The method of claim 1 wherein the content of the substance or combination of substances is presented on a display.

8. The method of claim 1 wherein at least one parameter for the dialysis treatment is adjusted depending on the measurement of the concentration of the substance or combination thereof.

9. The method of claim 8 wherein at least one parameter is adjusted manually.

10. The method of claim 8 wherein at least one parameter is adjusted automatically.

11. The method of claim 8 wherein the parameter which is adjusted is a blood flow in an extracorporeal blood path.

12. The method of claim 8 wherein the adjustment of the parameter for a dialysis machine by means of which a dialysis treatment is effected is adjusted continuously in relative to the measurement of the concentration.

13. The method of claim 7 wherein the effected measurement is presented on a printer.

* * * * *